US006860633B2

(12) United States Patent
Davis et al.

(10) Patent No.: US 6,860,633 B2
(45) Date of Patent: Mar. 1, 2005

(54) THERMAL EXPANSION MEASUREMENTS USING FABRY-PEROT ETALONS

(75) Inventors: Mark J. Davis, Clarks Summit, PA (US); Joseph S. Hayden, Clarks Summit, PA (US)

(73) Assignee: Schott Technologies, Inc., Duryea, PA (US)

( * ) Notice: Subject to any disclaimer, the term of this patent is extended or adjusted under 35 U.S.C. 154(b) by 88 days.

(21) Appl. No.: 09/997,219

(22) Filed: Nov. 30, 2001

(65) Prior Publication Data

US 2003/0103550 A1 Jun. 5, 2003

(51) Int. Cl.[7] .............................................. G01N 25/16
(52) U.S. Cl. .......................... 374/55; 374/43; 374/45
(58) Field of Search .............................. 374/55, 45, 43, 374/44

(56) References Cited

U.S. PATENT DOCUMENTS

| | | | | |
|---|---|---|---|---|
| 3,909,132 A | * | 9/1975 | Barrett | 356/45 |
| 3,938,889 A | * | 2/1976 | McKinnis | 356/109 |
| 4,775,214 A | * | 10/1988 | Johnson | 350/96.29 |
| 4,782,492 A | * | 11/1988 | McMahon et al. | 372/34 |
| 5,384,877 A | * | 1/1995 | Stone | 385/70 |
| 6,005,995 A | * | 12/1999 | Chen et al. | 385/24 |
| 6,101,201 A | * | 8/2000 | Hargis et al. | 372/36 |
| 6,186,937 B1 | * | 2/2001 | Ackerman et al. | 356/454 |
| 6,270,254 B1 | * | 8/2001 | Berthold et al. | 374/161 |
| 6,462,876 B1 | * | 10/2002 | O'Brien | 359/577 |
| 2002/0044574 A1 | * | 4/2002 | Abedin | 372/18 |
| 2003/0012250 A1 | * | 1/2003 | Shirasaki | 372/98 |
| 2003/0030908 A1 | * | 2/2003 | Cheng et al. | 359/577 |

FOREIGN PATENT DOCUMENTS

| | | | | |
|---|---|---|---|---|
| JP | 01119748 A1 | * | 5/1989 | 374/55 |
| JP | 01269040 A | * | 10/1989 | 374/55 |
| JP | 02017421 A | * | 1/1990 | 374/187 |

OTHER PUBLICATIONS

"Handbook of Optics" by the Optical Society of America, vol. 2, Sep. 1994, pp. 21.6–21.7.
Jacobs, "Dimensional Stability of Materials Useful in Optical Engineering", *Applied Optics and Engineering*, 1987, PP 71–107.
Hecht et al, *Optics*, Jun. 1974, pp. 307–311, Addison–Wesley Publ.

* cited by examiner

*Primary Examiner*—Diego Gutierrez
*Assistant Examiner*—Mirellys Jagan
(74) *Attorney, Agent, or Firm*—Millen, White, Zelano & Branigan, P.C.

(57) ABSTRACT

A method for determining the thermal expansion coefficient of a substance comprises, determining at each of two or more temperatures the absolute position of more than one resonant interference peaks of a Fabry-Perot etalon whose optical path is defined by said substance and calculating said coefficient from observed difference(s) in wavelength or frequency of said positions at said two or more temperatures.

22 Claims, 8 Drawing Sheets

THERMAL EXPANSION MEASUREMENTS USING FABRY-PEROT ETALONS

SUMMARY OF THE INVENTION

This invention relates to an improved method for high precision thermal expansion measurements, especially on small samples of low-expansion materials. Many of these are particularly useful in microlithographic applications.

This invention thus relates to a method for determining the thermal expansion coefficient of a substance comprising, determining at each of two or more temperatures the absolute position of more than one resonant interference peaks of a Fabry-Perot etalon whose optical path is defined by said substance, and calculating said coefficient from observed difference(s) in wavelength or frequency of said positions at said two or more temperatures.

The technique of this invention employs precise measurements of the resonant frequencies of Fabry-Perot etalons constructed from materials whose optical and physical properties are desired. A Fabry-Perot etalon for the present application can be implemented in two forms:
1. Solid forms: in which a single piece of glass, glass-ceramic, or other material with sufficient transmittance [T about 5% or higher] has a plano/plano polish and a reflecting coating (e.g., about 10% or higher) applied to its two ends; typically, very tight flatness and parallelism specs are involved (about $\lambda/20$ or greater flatness and <about 0.5 arc second or better parallelism).
2. Air-gap form: in which two transparent (e.g., about 10% or higher), flat and parallel coated plates (e.g., meeting the foregoing specs) "sandwich" a spacer having an area therein which creates an air gap. In this case, the material under test makes up the spacer which need not be transparent since the radiation traverses the air gap regions.

These solid etalons are of noncritical physical dimensions with typical cross section dimensions of, e.g., 5×3 mm with thickenesses of, e.g., 3 mm (in the direction of light propagation, typically "L" below). Air gaps are similarly sized with plate thickness of, e.g., 3 mm and "air" gaps of, e.g., 1 mm, 2mm, or more. Thus, sample sizes for the materials used in this invention can be very small (e.g., 0.1–10 mm) while maintaining high accuracy.

Etalons are commercially available from, e.g., Spectra Physics, Tec Optics, VLOC, (see, e.g., VLOC Models ES and EA). Typically, the best etalons will have high finesse (F) values, e.g., 10–1000; preferably, 100–1000; and high thermal insensitivity for the air gap versions, e.g., ±5 MHz shift over 0–70° C.

The solid etalon design allows for measurement of the "athermality" of a proposed athermal material, monolithic or composite, or of the low thermal expansion of a material. (A truly athermal material would have no change in optical length—the product of the material's physical length multiplied by its refractive index—following changes in temperature). The air-gap etalon design is also ideal for detecting temperature changes, thereby providing a means by which to very precisely measure thermal expansion on samples as small as 1 mm or smaller. The resultant thermal expansion data then enables calculations of other important parameters, e.g., estimates of dn/dt, where n is the index of refraction and T is the temperature.

Any material can be employed in this invention as either the solid etalon per se or as the test substance in the air-gap etalon as long as it is configurable to have the surface properties and transmittances mentioned above. Typical materials are glasses, glass-ceramics, amorphous and crystalline salts, polymers (organic and inorganic), composites (e.g., silicon, silicon carbide, sapphire, etc.) and metals, e.g., Invar. This invention especially relates to low expansion materials, e.g., having $\alpha_{0°-50°}$ of $0.1\times10^{-6}$/K, preferably $0.01\times10^{-6}$/K.

Precise radiation wavelengths used in the measurements are not critical and should be chosen in consideration of the corresponding transmittance of the material, available equipment, etc. Typically, wavelengths are in the range of UV, visible, near IR and IR. Unless indicated otherwise herein, conditions employed in the method of the invention are fully conventional in accordance with normal Fabry-Perot Etalon measurements.

The etalons enable thermal expansion measurements using basic relationships. Thus, the resonant frequencies of a Fabry-Perot etalon satisfy the following equation:

$$v_m = \frac{mc}{2nL}, \quad (1)$$

where $v_m$ is the m'th resonant frequency, m is an integer, c is the speed of light, n is the refractive index of the cavity material (e.g., glass, air vacuum or other material) and L is the cavity length. In wavelength units this constraint is written:

$$\lambda_m = \frac{2nL}{m}. \quad (2)$$

The spacing between resonances, also called the "free spectral range" (FSR), is given by:

$$\Delta v_{FSR} = \frac{c}{2Ln} \text{ or } \Delta\lambda_{FSR} = \frac{\lambda^2}{2Ln} \quad (3)$$

Figure 1:
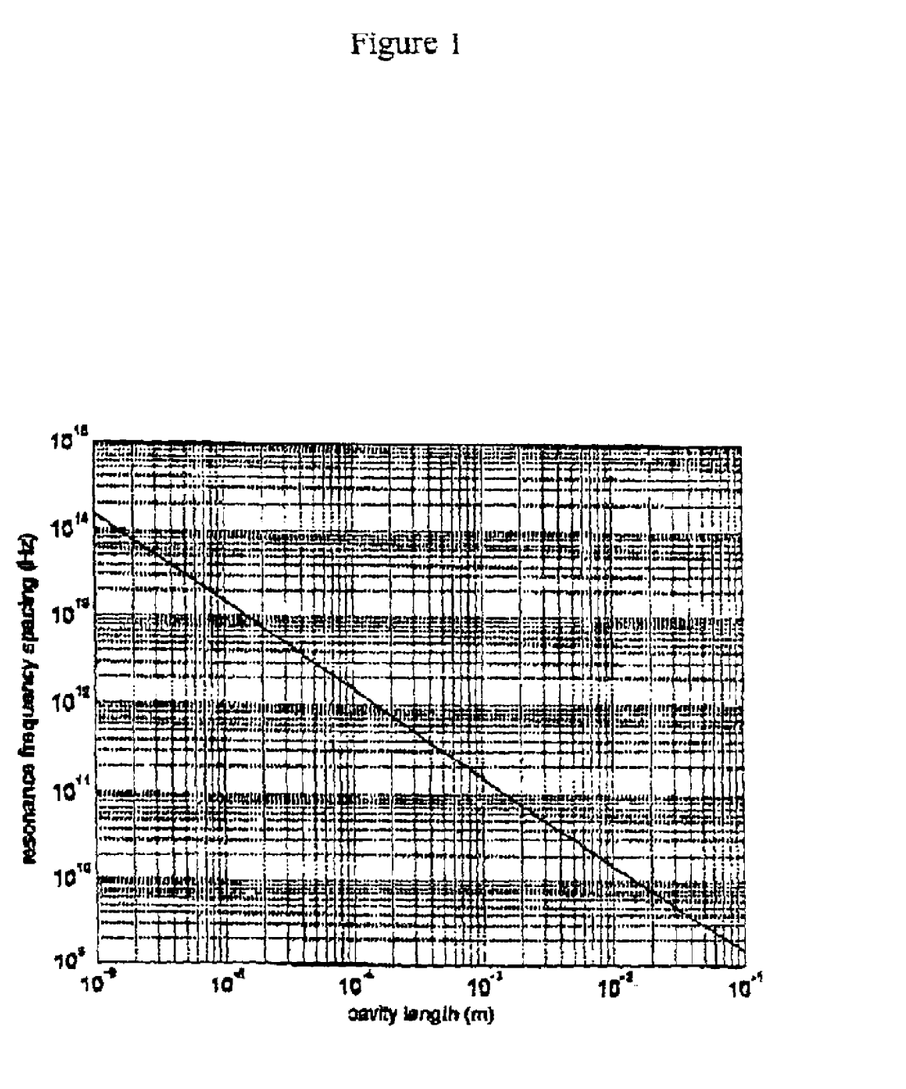
FIG. 1 illustrates the spacing between adjacent resonant frequencies (FSR) for a Fabry-Perot etalon as a function of cavity length.
Figure 2:
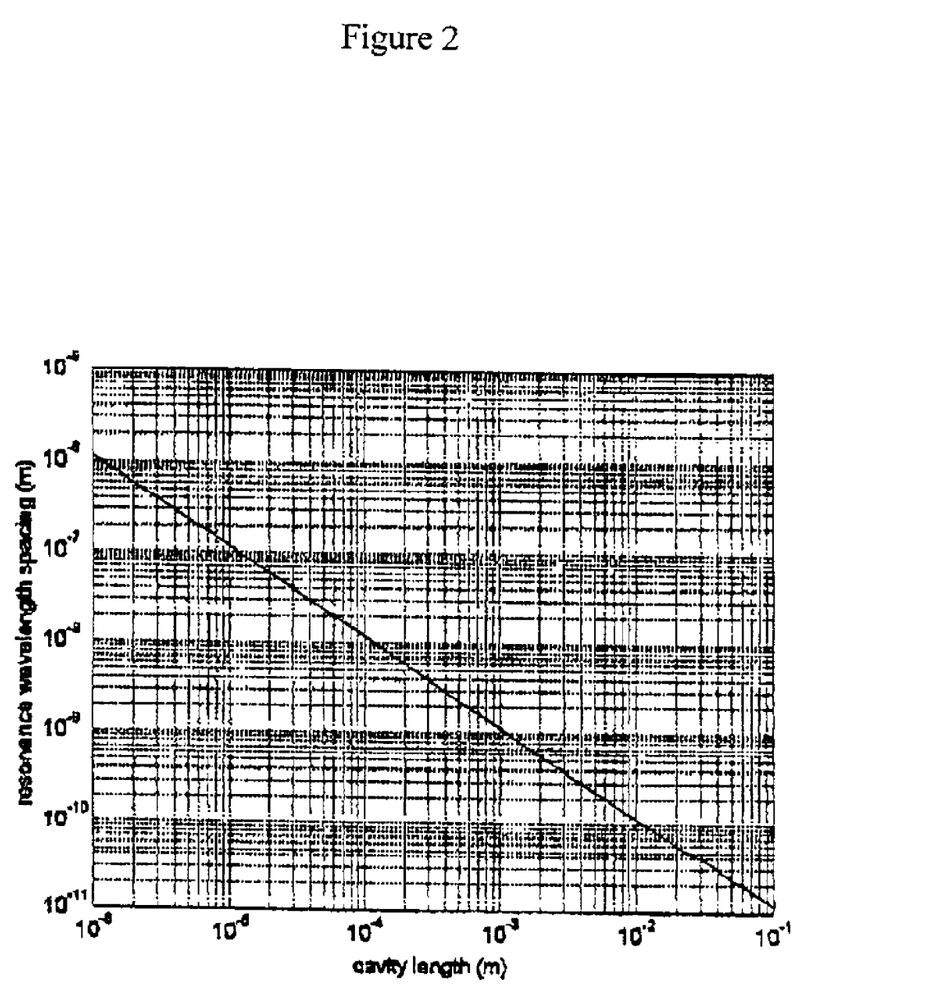
FIG. 2 illustrates the spacing between adjacent resonant wavelengths (FSR) for a Fabry-Perot etalon as a function of cavity length for a wavelength of 1550 nm.

These relations are shown in FIGS. 1 and 2 for cavity lengths between 1 $\mu$m and 100 mm.

The relation between the change in frequency position and change in length for a Fabry-Perot etalon is:

$$\Delta v = \frac{-v}{L}\Delta L, \quad (4)$$

whereas the relation between FSR and change in length is:

$$\Delta v_{FSR} = \frac{-c}{2L^2}\Delta L \quad (5)$$

Figure 3:
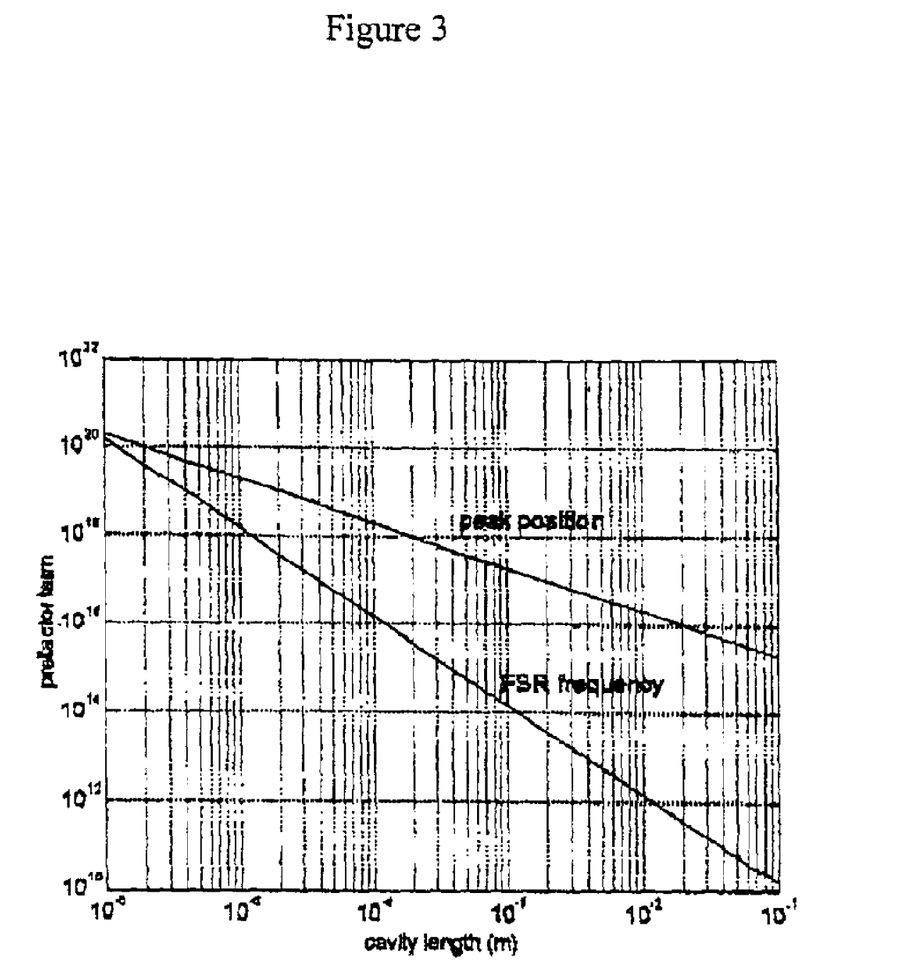
FIG. 3 illustrates the pre-factor terms that "convert" changes in length into changes in either resonant peak position or changes in FSR for a wavelength of 1550 nm (see Equations 4 and 5).

As an example, for a wavelength of 1550 nm (194 THz) and a cavity length of 1 mm, a 2 nm change in length would lead to only a 0.3 MHz change in FSR but a 387 MHz change in the position of the resonant frequencies. This can be seen most simply by evaluating the pre-factor terms on the RHS of equations 4 and 5 that multiply $\Delta L$. As shown in FIG. 3, for cavity lengths >10 $\mu$m, the pre-factor term for the absolute position of a resonant frequency is at least 10 times that for the change in FSR, all other quantities held constant. For a cavity length of 100 mm, the difference amounts to over $10^5$. This indicates that the most precise way in which to monitor changes in optical path length (nL) for a Fabry-Perot etalon is by precisely monitoring the absolute positions of one or more resonant frequencies. In essence, this optical setup "magnifies" very small changes in length into measurable changes in frequency. See, S. F. Jacobs, "Dimensional stability of materials useful in optical engineering"; 71–107 in *Applied Optics and Engineering*. Edited By R. R. Shannon, J. C. Wyant. Academic Press, San Diego, (1987).

Thus, this invention relates to determining or monitoring changes in the absolute frequencies of resonant peaks as a function of Fabry-Perot cavity length, i.e., as a function of temperature included length changes.

A number of implementations are possible for this invention, including the use of relatively high-power tunable lasers, e.g., Ti:sapphire lasers from Coherent Inc. or Spectra-Physics Lasers. Preferably, recent advances in instrumentation for the telecomm industry are employed, offering a relatively inexpensive and simpler solution. A multitude of companies offer tunable lasers, broadband optical power meters and optical signal analyzers designed to precisely characterize multiplexing filters, including DWDM thin-film interference filters. These offer a complete modular-based solution, including a tunable laser and power meters that are suitable for the present application.

Thus, a variety of light sources and detection equipment is applicable. For instance, tunable lasers are available in the preferred frequency range (about 1300–1700 nm, most preferably, 1460–1580 nm) with a resolution of (0.1 pm from Agilent Model 81680A), power meters from Agilent Model 81634A, optical signal analyzers from Burleigh, Model WA-7600. Optical configurations are routinely designed. See, e.g., Agilent Lightwave Test and Measurement 2001 Catalog.

For the solid etalon form, optical end surfaces are polished to the necessary specs using conventional techniques. See, e.g., Fabrication Methods for Precision Optics, Wiley, 1992. For the air gap form, the same is true for the end plate surfaces and the surfaces of the material placed in the "air gap" space. The plate and test material are placed together using optical contacting to ensure good measurements.

Figure 4:
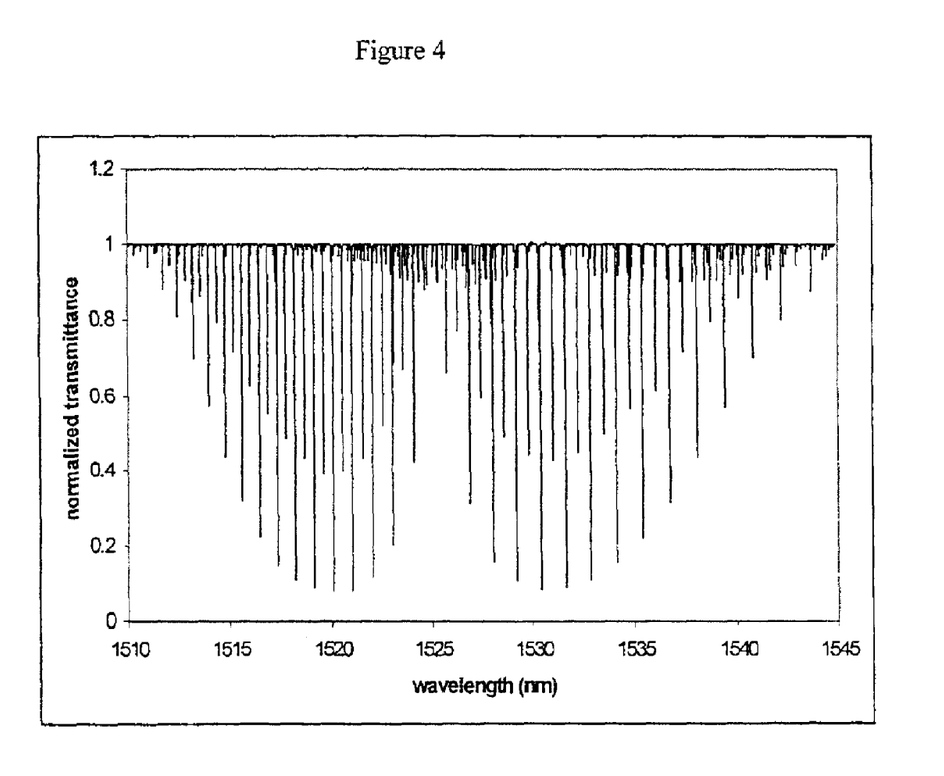
FIG. 4 shows a normalized spectrum of SRM 2517a obtained by scanning a tunable diode laser and measuring the laser power transmitted through an SRM unit.

As this method involves high-precision measurements of the absolute position of the resonant frequencies, preferably a very stable optical setup and/or wavelength standard is used for accurate $\Delta L/L$ measurements. To avoid the need for repeated drift corrections, the use of the NIST wavelength standard SRM 2517a is preferred. This standard consists of an enclosed quantity of low-pressure acetylene gas that exhibits over 50 very sharp and well-characterized vibrational absorbances in the wavelength range of 1510 to 1540 nm (FIG. 4). By splitting a laser beam into two parts, one to pass through the etalon and the other to go through the wavelength standard, and by simultaneously measuring absorbances in both optical paths, a well-defined set of "fiducial" marks can be overlaid onto the etalon-based resonances. This ensures knowledge of the precise wavelength scanned at any particular time by the tunable laser.

Figure 5:
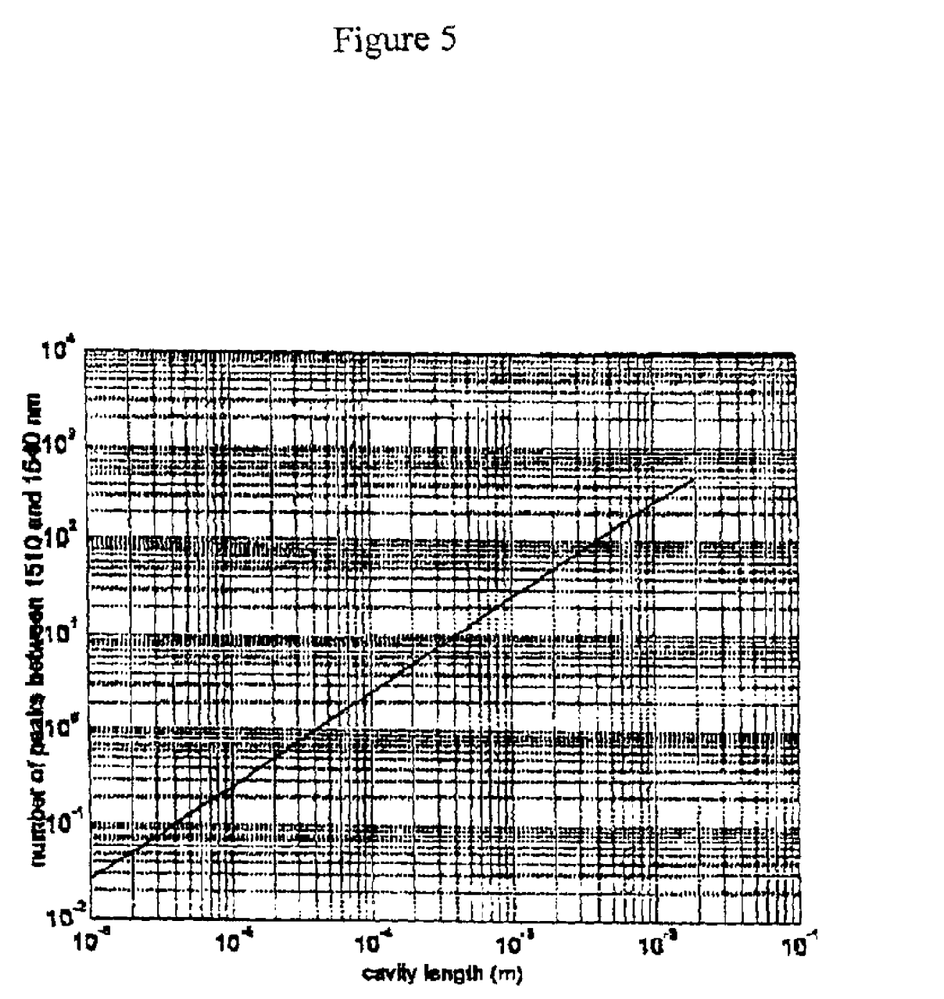
FIG. 5 illustrates the number of resonant peaks in the wavelength range 1510 to 1540 nm as a function of Fabry-Perot cavity length.

FIG. 5 shows the expected number of resonant frequency peaks in the range of 1510 to 1540 nm as a function of cavity length. This wavelength range is covered by the NIST standard. For example, a 1-mm cavity yields nearly 30 resonant peaks, whereas a 10-mm cavity yields over 250 peaks. In one option, the movement of all peaks is monitored against the background of fiducial marks provided by SRM 2517a, thereby providing for decreased statistical uncertainty in the measurement of frequency shifts. (Error is reduced proportional to $\sqrt{n}$, where n is the number of analyzed peaks.) Statistical calculations are fully conventional. Alternatively, a second temperature-stabilized Fabry-Perot etalon can be used to provide fiducial wavelength markings.

Figure 6:
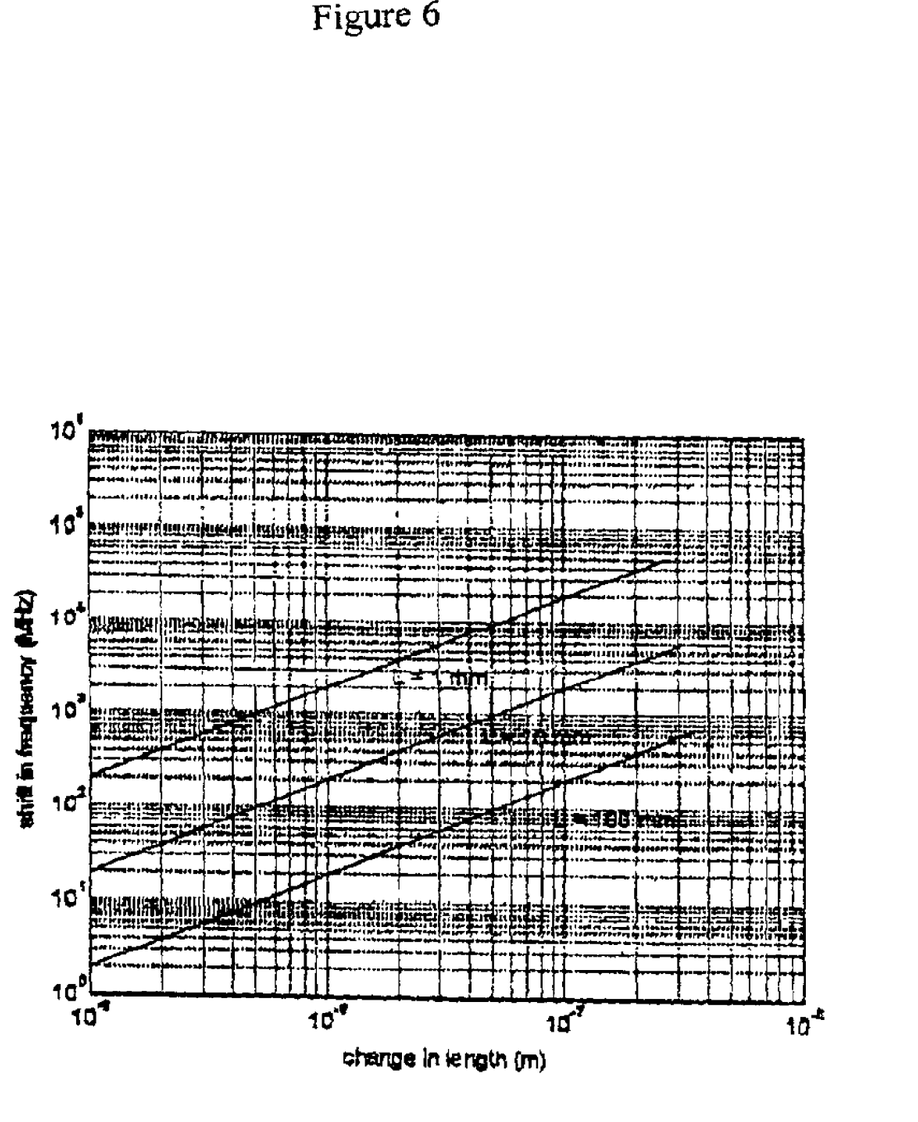
FIG. 6 demonstrates the expected shift in frequency position of 1, 10 and 100-mm thick etalons using a tunable laser at about 1550 nm subject to various changes in length (nm to Elm).

FIG. 6 shows the expected shift in frequency position of various etalons subject to changes in length in the range appropriate for both low and high-expansion materials.

For changes in length of 1 nm, a 1-mm cavity would yield a nearly 200 MHz shift, whereas a 100 mm cavity would yield only a 2 MHz shift. The sensitivity increases as the sample size decreases for a given displacement.

The "minimum resolvable bandwidth" in terms of frequency is given by (E. Hecht; A. Zajac, *Optics*. Reading, Mass., Addison-Wesley, 1974.):

$$\Delta v_{min} = \frac{c}{F2nL}, \quad (6)$$

where F is the "finesse" of the cavity, given alternatively by the ratio of the FSR to the full-width at half-max of the peaks or by (Handbook of Optics Vol. II, $2^{nd}$ edition, McGraw Hill, 1994):

$$F = \frac{\pi\sqrt{R}}{1-R}, \quad (7)$$

where R is the reflectance of the etalon's interior surfaces. Given typical achievable F-values from various vendors for commercial etalons (e.g., 1 to 1000; Spectra-Physics, VLOC), $\Delta v_{min}$ could range between 150 and 150,000 MHz for a 1 mm-thick etalon; for a 10 mm-thick etalon, these values would be 15 and 15,000 MHz. Thus, it is preferred to employ coatings wherever possible to maximize the finesse as much as possible for the most precise frequency shift measurements. Given a 10 mm-thick etalon and coatings to allow a finesse approaching 1000, a change in length of 1 nm should be just discernible. It is also possible to use multiple peaks, e.g., all 250 that would be observable within the NIST standard range for a 10-mm thick etalon. This would reduce the uncertainty in observable frequency shift by a factor of ~15.

Spectra-Physics specs its "thermally-insensitive" air-gap etalons with a ±2 MHz thermal stability in the temperature range of 0 to 70° C. Given a cavity length of 3 mm, this corresponds to a measurement of the change in optical path length in the range of 0.6 nm. Thus, the method of the invention in this case is capable of quantifying the change in optical path length with temperature to a high level.

Moreover, considering the governing equation for a solid etalon:

$$\frac{dOPL}{dT} = L_o\left(\frac{dn}{dT} + \alpha n\right), \quad (8)$$

where OPL is the optical path length, T is temperature and $\alpha$ is the linear thermal expansion coefficient measured in accordance with this invention, it is possible also to calculate dn/dT. Independent measurements of n, $L_o$, and $\alpha$ are required. These are generally much easier to measure than dn/dT.

BRIEF DESCRIPTION OF THE DRAWINGS

to better visualize the overlap between the absorption peaks of the reference cell and the transmission peaks of the sample etalon.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications cited above are hereby incorporated by reference.

EXAMPLE

Two 2.3-mm air-gap etalons have reflectances of 0.65 and 0.95, corresponding to theoretical finesses of 7.24 and 61.2, respectively. Optical test equipment for the measurements includes the following Agilent models: 81680A (tunable laser); 81634A (power sensor module); and 8164A (system mainframe). A NIST acetylene cell is incorporated as a wavelength reference.

Figure 7A:
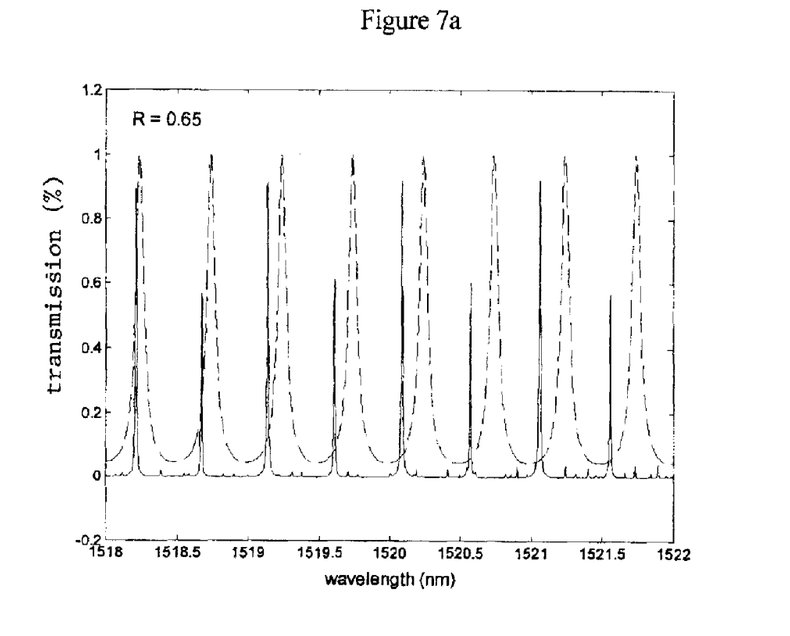
FIGS. 7a and 7b ((a) F-7.24; (b) F-61.2) show the spectral response (normalized transmission) of an acetylene cell (solid line) and sample etalon (dashed line). Acetylene data are plotted as $$\left(1 - \frac{\text{transmission}}{100}\right)$$
Figure 7B:
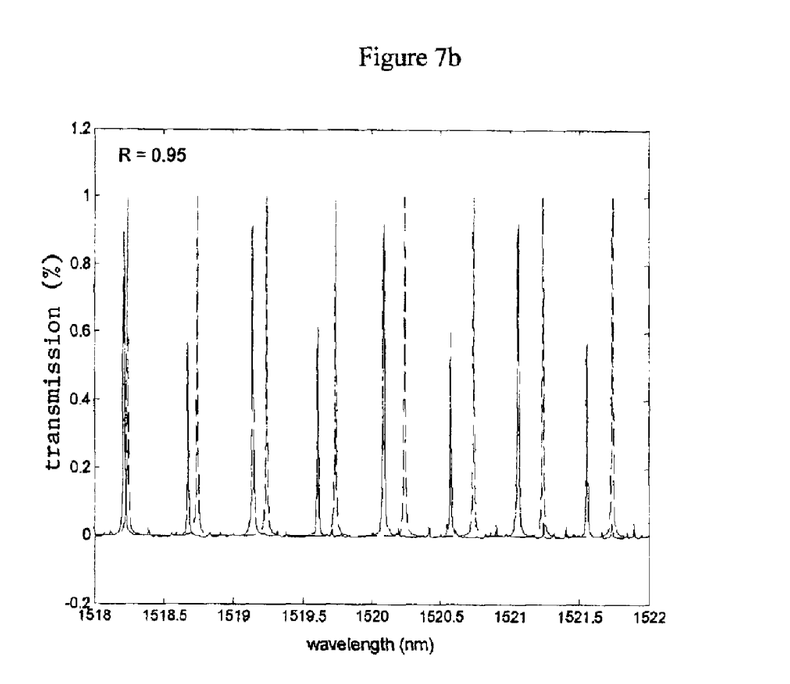

FIG. 7 shows the calculated spectral responses of both the NIST acetylene cell and the sample etalons in the spectral range of 1518 to 1522 nm.

For this given set of conditions (air as the test material), the spacings of peak transmission of the sample etalon nearly coincides with those of the main absorption peaks of acetylene (about 0.6 nm spacing, or 77 GHz), thereby providing multiple reference peaks for improved accuracy. One could, in practice, use 10's of peaks of both the sample etalon and the reference cell to greatly improve measurement precision. With the presence of an absolute reference cell in the form of either the NIST cell or a temperature-stabilized Fabry-Perot reference cell, good measurement accuracy is assured.

In practice, at each time ($\Delta T$) increment of interest, itself determined by the accuracy required for a given material's thermal expansion and favored heating rate, the laser scans across the entire wavelength region of interest (10's of nm). Given the small sample sizes emphasized in this invention, heating rates exceeding 1° C./min are easily attainable using commercially available equipment. Conventional data analysis (in near real-time or after the completion of an entire thermal scan) is conducted to place constraints on the absolute positions of the etalon peaks relative to the "fiducial marks" defined by the reference cell. This process is repeated for each scan. Differences between time-adjacent ($\Delta T$) scans are calculated using recorded data, which in turn are used to calculate thermal expansions using equation (4) and the measured temperature change of the sample etalon.

Figure 8A:
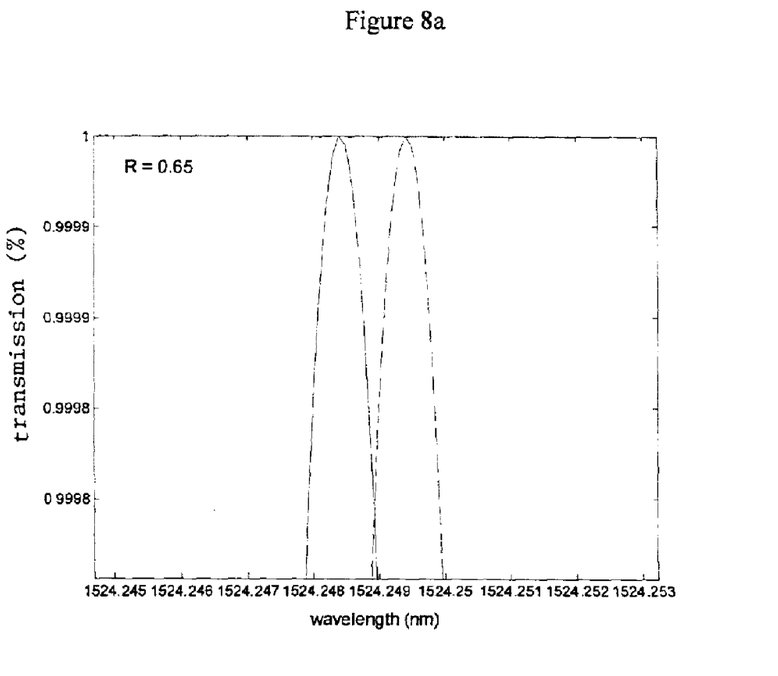
FIGS. 8a and 8b ((a) F-7.24; (b) F-61.2)) show the shift in peak position before (solid line) and after (dashed line) a 1-nm change in sample length (normalized transmission).
Figure 8B:
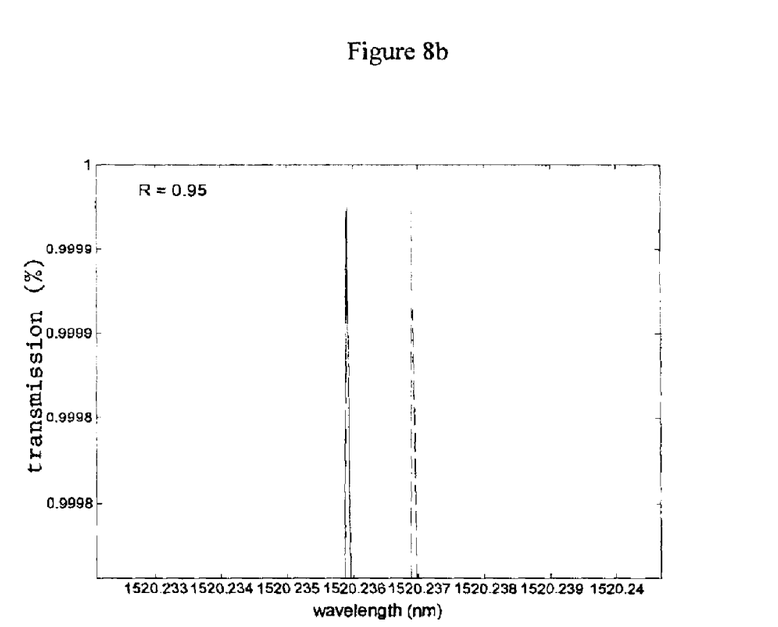

FIG. 8 shows the calculated change in peak position for an etalon peak following a ~1 nm change in sample length for the two etalons under consideration.

For the higher finesse etalon (b), the two peaks are well separated (~1 pm), whereas for the lower finesse etalon, the two peaks overlap at very nearly the peak transmittance, demonstrating the preference for higher finesses. Similar peak positions changes are obtained for test material under corresponding conditions (e.g., thickness of 2.3 mm, $\Delta T$~8° C. and coefficient of thermal expansion (=0.05×10$^{-6}$/K).

At the conclusion of the entire scan, the entire record of thermal expansion is available for the etalon under question. Using fully conventional considerations, such data concerning $\Delta L$ vs $\Delta T$ is used to determine coefficients of thermal expansion.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for determining the thermal expansion coefficient of a substance comprising:
   determining at each of two or more temperatures the absolute position in wavelength or frequency represented by multiple resonant interference peaks of a Fabry-Perot etalon whose optical path is defined by said substance and calculating a value of said coefficient from calculated difference(s) in said wavelengths or frequencies at said two or more temperatures, said difference(s) being calculated statistically from said multiple resonant interference peaks.

2. A method of claim 1, where frequency positions are measured.

3. A method of claim 1, wherein wavelength positions are measured.

4. A method of claim 1, wherein said Fabry-Perot etalon consists essentially of a solid sample of said substance having highly flat end surfaces.

5. A method of claim 1, wherein said Fabry-Perot etalon comprises an optical path consisting essentially of said substance and at the ends thereof highly flat plates of a different material.

6. A method of claim 1, wherein the change in length ($\Delta L$) of said substance at two different temperatures is calculated from the differences ($\Delta v$) in the absolute position in frequency represented by multiple resonant interference peaks by the equation:

$$\Delta v = \frac{-v}{L} \Delta L, \quad (4)$$

where L is the Fabry-Perot gap at the first temperature and v is the frequency position of the respective peak at said temperature.

7. A method of claim 1, the frequency peak positions are in the range of 1300–1700 nm.

8. A method of claim 1, wherein the end surfaces of the etalon has λ/20 flatness or better and <0.5 arc second parallelism or better.

9. A method of claim 1, wherein the number of said peak positions measured is ten or more.

10. A method of claim 1, wherein the finesse of the etalon is 1–1000.

11. A method for determining the thermal expansion coefficient of a substance comprising:

determining at each of two or more temperatures the absolute position in wavelength or frequency represented by multiple resonant interference peaks of a Fabry-Perot etalon whose optical path is defined by said substance and calculating a value of said coefficient from calculated difference(s) in said wavelengths or frequencies at said two or more temperatures, wherein said absolute positions are determined by simultaneous reference to a standard having multiple fiducial marks which are overlaid onto etalon based resonances, said difference(s) being calculated statistically from said multiple resonant interference peaks.

12. A method of claim 11, wherein the reference standard is a gas standard or a temperature-stabilized Fabry-Perot etalon.

13. A method of claim 11, where frequency positions are measured.

14. A method of claim 11, wherein wavelength positions are measured.

15. A method of claim 11, wherein said Fabry-Perot etalon consists essentially of a solid sample of said substance having highly flat end surfaces.

16. A method of claim 11, wherein said Fabry-Perot etalon comprises an optical path consisting essentially of said substance and at the ends thereof highly flat plates of a different material.

17. A method of claim 11, wherein the change in length (ΔL) of said substance at two different temperatures is calculated from the differences (Δv) in the absolute position in frequency represented by multiple resonant interference peaks by the equation:

$$\Delta v = \frac{-v}{L} \Delta L, \quad (4)$$

where L is the Fabry-Perot gap at the first temperature and v is the frequency position of the respective peak at said temperature.

18. A method of claim 11, wherein the frequency peak positions are in the range of 1300–1700 nm.

19. A method of claim 11, wherein the end surfaces of the etalon has λ/20 flatness or better and <0.5 arc second parallelism or better.

20. A method of claim 11, wherein the finesse of the etalon is 1–1000.

21. A method for determining the thermal expansion coefficient of a substance comprising:

determining at each of two or more temperatures the absolute position in wavelength or frequency represented by ten or more resonant interference peaks of a Fabry-Perot etalon whose optical path is defined by said substance and calculating a value of said coefficient from calculated difference(s) in said wavelengths or frequencies at said two or more temperatures, wherein said absolute positions are determined by simultaneous reference to a standard having multiple fiducial marks which are overlaid onto etalon based resonances, said difference(s) being calculated statistically from said multiple resonant interference peaks.

22. A method of claim 21, wherein the reference standard is a gas standard or a temperature-stabilized Fabry-Perot etalon.

* * * * *